(12) United States Patent
High

(10) Patent No.: US 8,773,648 B2
(45) Date of Patent: Jul. 8, 2014

(54) IMAGING SYSTEM WITH MOTORIZED POSITIONING OF IMAGE CAPTURE DEVICE

(71) Applicant: Gemvision Corporation, L.L.C., Davenport, IA (US)

(72) Inventor: Jeffrey L. High, Lafayette, LA (US)

(*) Notice: Subject to any disclaimer, the term of this patent is extended or adjusted under 35 U.S.C. 154(b) by 0 days.

(21) Appl. No.: 13/770,580

(22) Filed: Feb. 19, 2013

(65) Prior Publication Data

US 2013/0329212 A1   Dec. 12, 2013

Related U.S. Application Data

(60) Provisional application No. 61/600,450, filed on Feb. 17, 2012.

(51) Int. Cl.
  *G01N 21/00*   (2006.01)
(52) U.S. Cl.
  USPC ............................................. 356/30
(58) Field of Classification Search
  CPC ...................................................... G01N 21/87
  USPC ...................................................... 356/30–31
  See application file for complete search history.

(56) References Cited

U.S. PATENT DOCUMENTS

| | | | |
|---|---|---|---|
| 6,552,300 B1 | 4/2003 | Kerner | |
| 6,567,156 B1 | 5/2003 | Kerner | |
| 7,414,709 B2 | 8/2008 | Wagner et al. | |
| 7,436,498 B2 | 10/2008 | Kerner et al. | |
| 8,116,552 B2 | 2/2012 | Lapa et al. | |
| 2003/0107722 A1 | 6/2003 | Klingler | |
| 2005/0190357 A1 | 9/2005 | Sasian et al. | |
| 2006/0232764 A1 | 10/2006 | Altman | |
| 2010/0111354 A1* | 5/2010 | Hornabrook et al. | 382/100 |
| 2011/0228063 A1 | 9/2011 | Smith et al. | |

OTHER PUBLICATIONS

ISR received by Applicant in co-pending PCT application having serial No. PCT/US2013/026720; to be published Aug. 19, 2013; submitted in its entirety.

* cited by examiner

*Primary Examiner* — Tara S Pajoohi Gomez
(74) *Attorney, Agent, or Firm* — Hamilton IP Law, PC; Jay R. Hamilton; Charles A. Damschen

(57) ABSTRACT

An imaging system may be collect information related to a specific gemstone such that a user may later access those images in a manner that allows the user to emulate a microscope. The illustrative embodiment of the imaging system may allow a subject gemstone to be rotated by 360 degrees in yaw, pitch, and roll dimensions relative to an image capture device, and the linear distance between the image capture device and the subject gemstone to be adjusted. The illustrative embodiment of the image capture device may record images of the subject gemstone at a plurality of focal points in three-dimensional space from a plurality of angles. A viewer system may be used to access images for a specific gemstone.

12 Claims, 11 Drawing Sheets

IMAGING SYSTEM WITH MOTORIZED POSITIONING OF IMAGE CAPTURE DEVICE

CROSS-REFERENCE TO RELATED APPLICATIONS

This application claims priority under 35 U.S.C. §119(e) of provisional U.S. Pat. App. Ser. No. 61/600,450 filed on Feb. 17, 2012, which is incorporated by reference herein in its entirety.

FIELD OF THE INVENTION

The present invention relates to an imaging system and viewer system for capturing and reproducing images and/or videos of objects obtained through an image capture device.

STATEMENT REGARDING FEDERALLY SPONSORED RESEARCH OR DEVELOPMENT

No federal funds were used to develop or create the invention disclosed and described in the patent application.

REFERENCE TO SEQUENCE LISTING, A TABLE, OR A COMPUTER PROGRAM LISTING COMPACT DISK APPENDIX

Not Applicable.

AUTHORIZATION PURSUANT TO 37 C.F.R. §1.71 (D)

A portion of the disclosure of this patent document contains material which is subject to copyright and trademark protection. The copyright owner has no objection to the facsimile reproduction by anyone of the patent document or the patent disclosure, as it appears in the Patent and Trademark Office patent file or records, but otherwise reserves all copyrights whatsoever.

BRIEF DESCRIPTION OF RELATED TECHNOLOGY

Various devices exist that attempt to objectify traditionally subjective characteristics of gemstones and other diamonds. For example, U.S. Pat. No. 8,116,552, directed to an apparatus for determining light properties of a diamond, uses compares specific portions of an image under different lighting characteristics. Similarly, U.S. Pat. No. 7,414,709 is directed to evaluating the light performance of a gemstone. Both patents are incorporated by reference herein in their entireties.

DETAILED DESCRIPTION

Brief Description of Drawings

In order that the advantages of the invention will be readily understood, a more particular description of the invention briefly described above will be rendered by reference to specific embodiments illustrated in the appended drawings. Understanding that these drawings depict only typical embodiments of the invention and are not therefore to be considered limited of its scope, the invention will be described and explained with additional specificity and detail through the use of the accompanying drawings.

Figure 1:
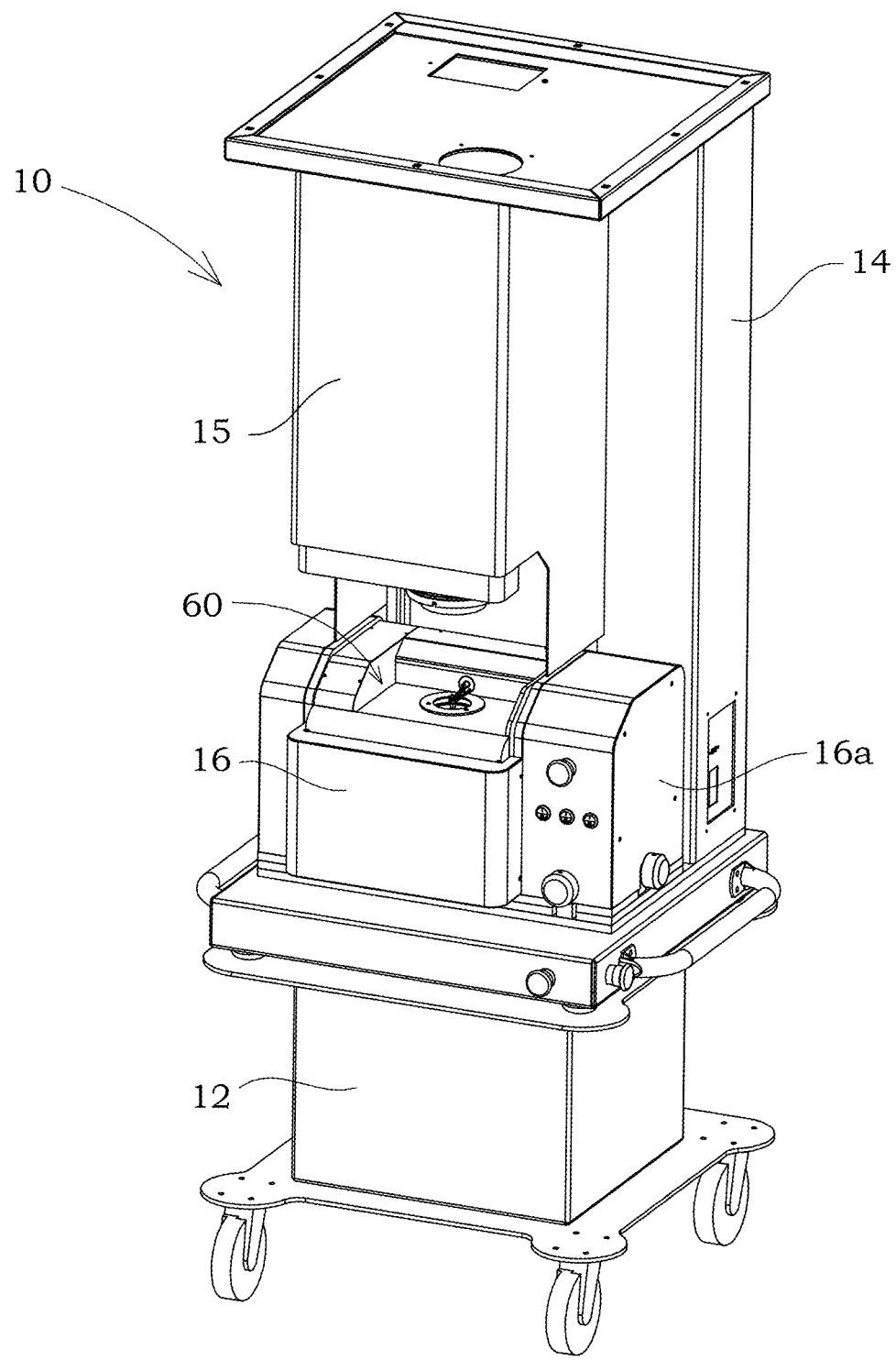
FIG. 1 provides a front perspective view of the illustrative embodiment of an imaging system.

| DETAILED DESCRIPTION—LISTING OF ELEMENTS | |
|---|---|
| Element Description | Element Number |
| Imaging system | 10 |
| Chassis | 12 |
| Tower | 14 |
| Front cover | 15 |
| Base cover | 16 |
| Base side cover | 16a |
| Switch | 17 |
| Conduit | 18 |
| Image capture device | 20 |
| Capture device bracket | 22 |
| Capture device track | 24 |
| Capture device bracket positioner | 26 |
| Lens | 30 |
| Bellows | 31 |
| Lens bracket | 32 |
| Lens track | 34 |
| Lens bracket positioner | 36 |
| Illuminator | 40 |
| Illuminator segment | 41 |
| Illuminator bracket | 42 |
| Illuminator track | 44 |
| Illuminator bracket positioner | 46 |
| Base | 50 |
| Base plate | 51 |
| X-axis plate | 52 |
| X-axis adjustor | 52a |
| Y-axis plate | 54 |
| Y-axis adjustor | 54a |
| First mount | 55 |
| Second mount | 56 |
| First axis | 58 |
| Stage | 60 |
| Bottom illuminator | 61 |
| Main platform | 62 |
| Aperture | 62a |
| Holder | 63 |
| Belt | 63a |
| Yaw motor | 63b |
| Holder tip | 63c |

-continued

DETAILED DESCRIPTION—LISTING OF ELEMENTS

| Element Description | Element Number |
| --- | --- |
| Holder mount | 64 |
| Yaw motor mount | 64a |
| Rotor | 65 |
| Rotor arm | 65a |
| Rotor bracket | 65b |
| Receiver | 65c |
| Roll motor | 66 |
| Rotor belt | 66a |
| Stage pivot point | 67 |
| Pitch motor | 67a |
| Back plate | 68 |
| Side plate | 68a |
| Tab | 68b |
| Viewer system | 100 |
| Database | 102 |
| User device | 104 |
| GUI | 110 |
| Main pane | 112 |
| Orientation indicator | 114 |
| Focal depth line | 114a |
| Image selector | 115 |
| Video pane | 116 |
| Tool selector | 118 |
| Zoom in | 118a |
| Zoom out | 118b |
| Pan | 118c |
| Markup | 118d |

Before the various embodiments of the present invention are explained in detail, it is to be understood that the invention is not limited in its application to the details of construction and the arrangements of components and elements set forth in the following description or illustrated in the drawings. The invention is capable of other embodiments and of being practiced or of being carried out in various ways not explicitly disclosed herein without departing from the scope and spirit of the present invention.

DETAILED DESCRIPTION OF INVENTION

Before the various embodiments of the present invention are explained in detail, it is to be understood that the invention is not limited in its application to the details of construction and the arrangements of components set forth in the following description or illustrated in the drawings. The invention is capable of other embodiments and of being practiced or of being carried out in various ways. Also, it is to be understood that phraseology and terminology used herein with reference to device or element orientation (such as, for example, terms like "front", "back", "up", "down", "top", "bottom", and the like) are only used to simplify description of the present invention, and do not alone indicate or imply that the device or element referred to must have a particular orientation. In addition, terms such as "first", "second", and "third" are used herein and in the appended claims for purposes of description and are not intended to indicate or imply relative importance or significance.

The following detailed description is of the best currently contemplated modes of carrying out illustrative embodiments of the invention. The description is not to be taken in a limiting sense, but is made merely for the purpose of illustrating the general principles of the invention, since the scope of the invention is best defined by the appending claims.

1. General Description of Components

Various inventive features are described below that can each be used independently of one another or in combination with other features. Broadly, an embodiment of the imaging system 10 and associated method may provide an apparatus and method of capturing images and/or video of a selected gemstone in high resolution with three hundred and sixty degree (360°) viewing angles, as well as a method for retrieval and viewing of the captured images and/or video such that the end user may manipulate the images and/or video so as to emulate a microscope. The images and/or video may be stored in a remote location (such as a file server, database, or other electronic storage device) so that they may be accessed from a different location and/or from multiple locations that are geographically disparate (such as through the Internet, a wide area network (WAN), and/or local area network (LAN)). That is, the illustrative embodiment of the imaging system 10 and associated method may allow a user to remotely access images and/or video of a particular gemstone via a computer such that the user may evaluate the gemstone as the same level as if the user had physical possession of the gemstone and was viewing it through a microscope.

As shown in FIG. 1, which provides a perspective view of the illustrative embodiment of the imaging system, the illustrative embodiment of an imaging system 10 as shown herein may include a tower 14 engaged with a base 50. The base 50 may be engaged with a chassis 12, as shown herein, wherein the chassis 12 is configured with wheels to allow easy movement of the imaging system 10. Alternatively, the base 50 may be positioned directly onto a countertop or other suitable structure. It is contemplated that the subject gemstone may be positioned on a stage 60, which stage 60 in turn may be engaged with the base 50.

Still referring to FIG. 1, the tower 14 may include a front cover 15, which may function to protect various internal components of the tower 14 from the external environment. Likewise, the base 50 may include a base cover 16 and one or more base side covers 16a to protect various internal components of the base 50 form the external environment. Generally, the tower 14 may be configured so that it is positioned above the base 50.

Figure 2A:
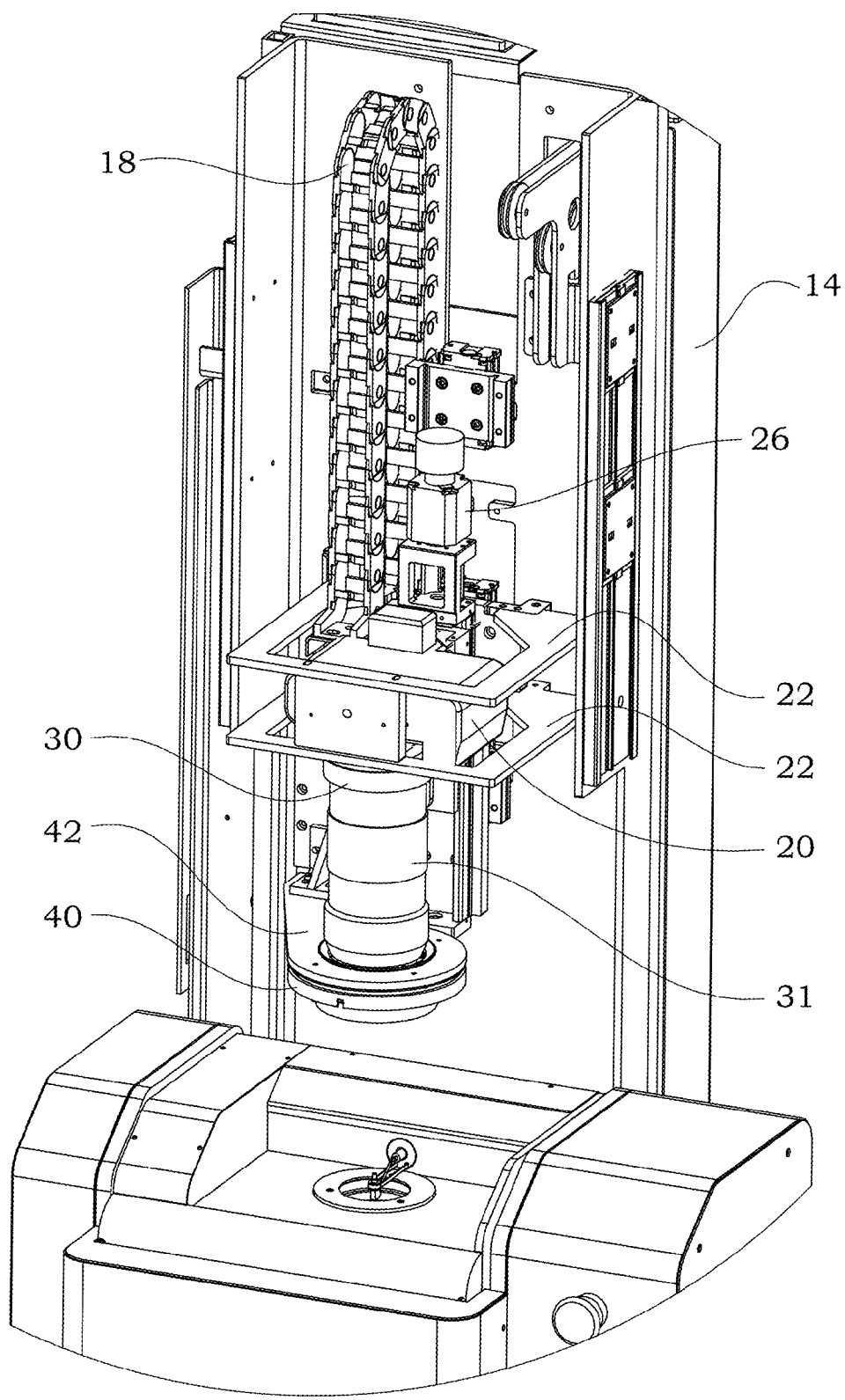
FIG. 2A provides a detailed front perspective view of the upper portion of the illustrative embodiment of an imaging system with the front cover removed.

Several components that may be positioned in the tower 14, some of which are shown in FIG. 2A. In the illustrative embodiment of the imaging system 10 as shown herein, an image capture device 20, lens 30, and illuminator 40 may be engaged with the tower 14. In this embodiment, the image capture device 20, lens 30, and illuminator 40 are configured such that each may move vertically along a portion of the height of the tower 14 independent of one another. A bellows 31 may be used to control the amount/intensity of light passing between the image capture device 20 and the lens 30, the lens 30 and the illuminator 40, and/or the image capture device 20 and the illuminator 40. In the illustrative embodiment shown in FIG. 2A, a bellows 31 is shown positioned between the lens 30 and the illuminator 40. Accordingly, the lighting conditions at the lens 40 may be controlled by the user.

Figure 2B:
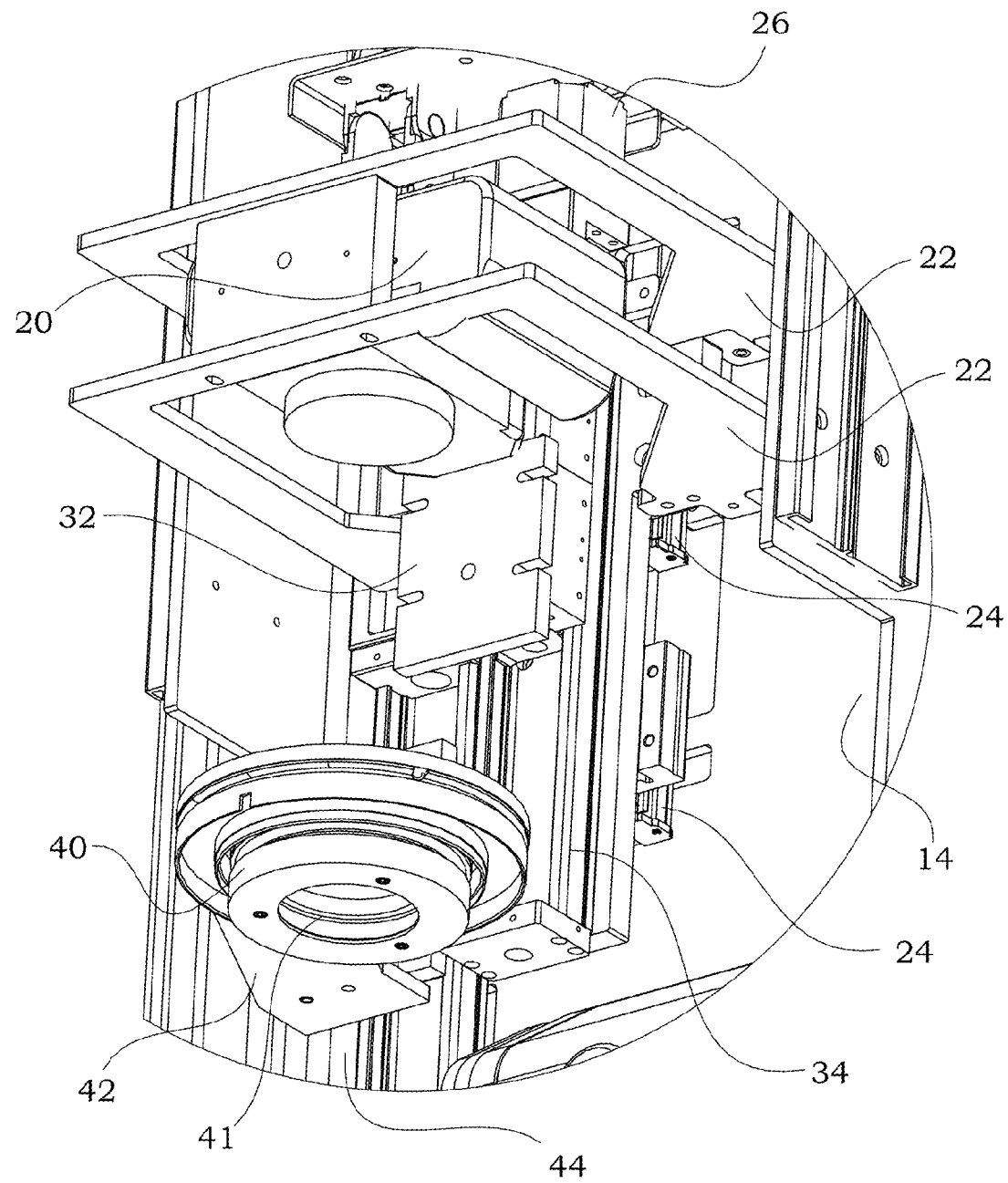
FIG. 2B provides a detailed front perspective view of the upper portion of the illustrative embodiment of an imaging system with the front cover and bellows removed.
Figure 2C:
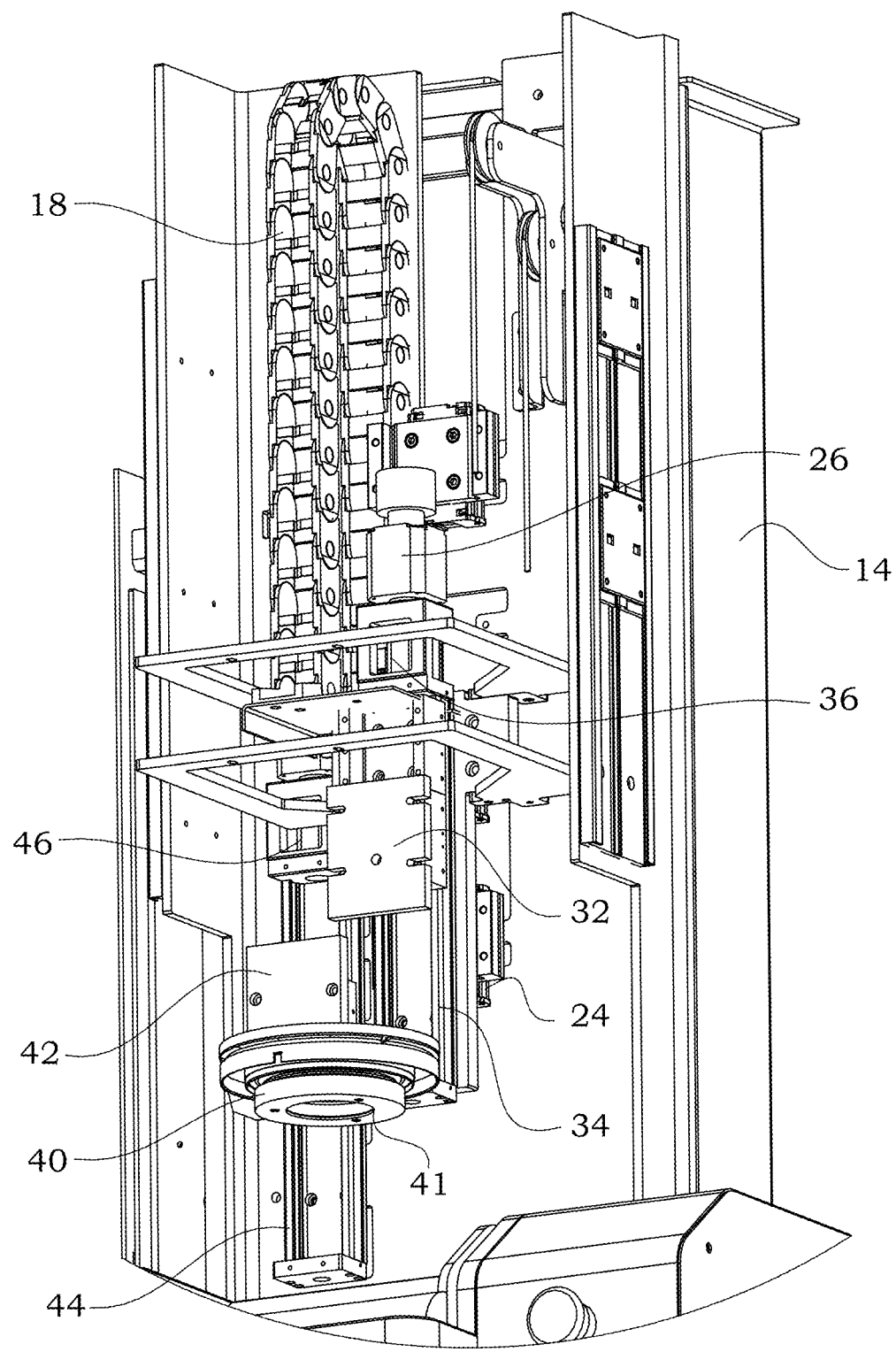
FIG. 2C provides a detailed perspective view of the upper portion and various positioners of the illustrative embodiment of an imaging system.

One configuration that allows this independent movement is best shown in FIGS. 2B & 2C. As shown, the illuminator 40 may be engaged with an illuminator bracket 42 such that the illuminator 40 may move with the illuminator bracket 42. The illuminator bracket 42 may be slideably engaged with an illuminator track 44, as best shown in FIG. 2C. An illuminator bracket positioner 46 may be engaged with the illuminator bracket 42 and serve to communicate a motive force to the illuminator bracket 42 sufficient to affect the linear position of the illuminator bracket 42 along the illuminator track 44. It is contemplated that the illuminator bracket positioner 46 may be electrically powered, but the imaging system 10 as disclosed and claimed herein is not so limited, and includes any suitable type of illuminator bracket positioner 46 that functions to adjust the position of the illuminator bracket 42 along the length of the illuminator track 44.

The illuminator 40 may be comprised of one or more illuminator segments 41, wherein each illuminator segment 41 may provide different lighting conditions. For example, for certain applications it may be advantageous for a first illuminator segment 41 to emit a first color of light (e.g., 6300K) from a first angle with respect to a gemstone and a second illuminator segment 41 to emit a second color of light (e.g., 4700K) from a second angle with respect to a gemstone. The illuminator 40 may use any type of light emitting source, including but not limited to LEDs, incandescent light bulbs, fluorescent light bulbs, IR light emitters, and/or combinations thereof. Additionally, illuminator segments 41 may be any shape suitable for the specific application of the imaging system 10. For example, in one embodiment the illuminator segments 41 may be linear, while in another embodiment the illuminator segments 41 may be round and/or curved. Accordingly, the specific shape of an illuminator segment 41 in no way affects the scope of the imaging system 10 as disclosed and claimed herein.

Again referring to FIGS. 2B & 2C, an image capture device 20 may be engaged with a capture device bracket 22 such that the image capture device 20 may move with the capture device bracket 22. The capture device bracket 22 may be slideably engaged with a capture device track 24, as best shown in FIG. 2B. A capture device bracket positioner 26 may be engaged with the capture device bracket 22 and serve to communicate a motive force to the capture device bracket 22 sufficient to affect the linear position of the capture device bracket 22 along the capture device track 24. It is contemplated that the capture device bracket positioner 26 may be electrically powered, but the imaging system 10 as disclosed and claimed herein is not so limited, and includes any suitable type of capture device bracket positioner 26 that functions to adjust the position of the capture device bracket 22 along the length of the capture device track 24.

The capture device bracket 22 as shown in the illustrative embodiment of the imaging system 10 may be comprised of several pieces working in concert. For example, FIG. 2C provides a clear view of two distinct capture device brackets 22, between which the image capture device 20 may be secured (as shown in FIG. 2B). Additionally, and as described in detail below, the capture device bracket 22 may be engaged with the lens track 34 and/or be formed therewith.

Still referring to FIGS. 2B & 2C, a lens 30 may be engaged with a lens bracket 32 such that the lens 30 may move with the lens bracket 32. The lens bracket 32 may be slideably engaged with a lens track 34, as best shown in FIG. 2C. A lens bracket positioner 36 may be engaged with the lens bracket 32 and serve to communicate a motive force to the lens bracket 32 sufficient to affect the linear position of the lens bracket 32 along the lens track 34. It is contemplated that the capture device bracket positioner 26 may be electrically powered, but the imaging system 10 as disclosed and claimed herein is not so limited, and includes any suitable type of capture device bracket positioner 26 that functions to adjust the position of the capture device bracket 22 along the length of the capture device track 24.

In certain applications for the imaging system 10 it may be advantageous for the distance between the lens 30 and the image capture device 20 to remain constant, even when the position of the image capture device 20 changes. To accomplish such functionality, the lens track 34 may be engaged with the capture device bracket 22, as in the illustrative embodiment of the imaging system 10. Alternatively, the capture device bracket 22 may be integrally formed with the lense track 34 so as to more therewith. Accordingly, when the capture device bracket 22 moves along the capture device track 24, the lens 30, lens bracket 32, lens track 34, and lens bracket position 36 may move with the capture device bracket 22 to ensure that the proper orientation is maintained between the image capture device 20 and the lens 30. This may be especially desirable when the image capture device 20 and lens 30 are focused for a particular distance from the lens 30, and the user desires to capture images of a gemstone at different depths within the gemstone.

Figure 3A:
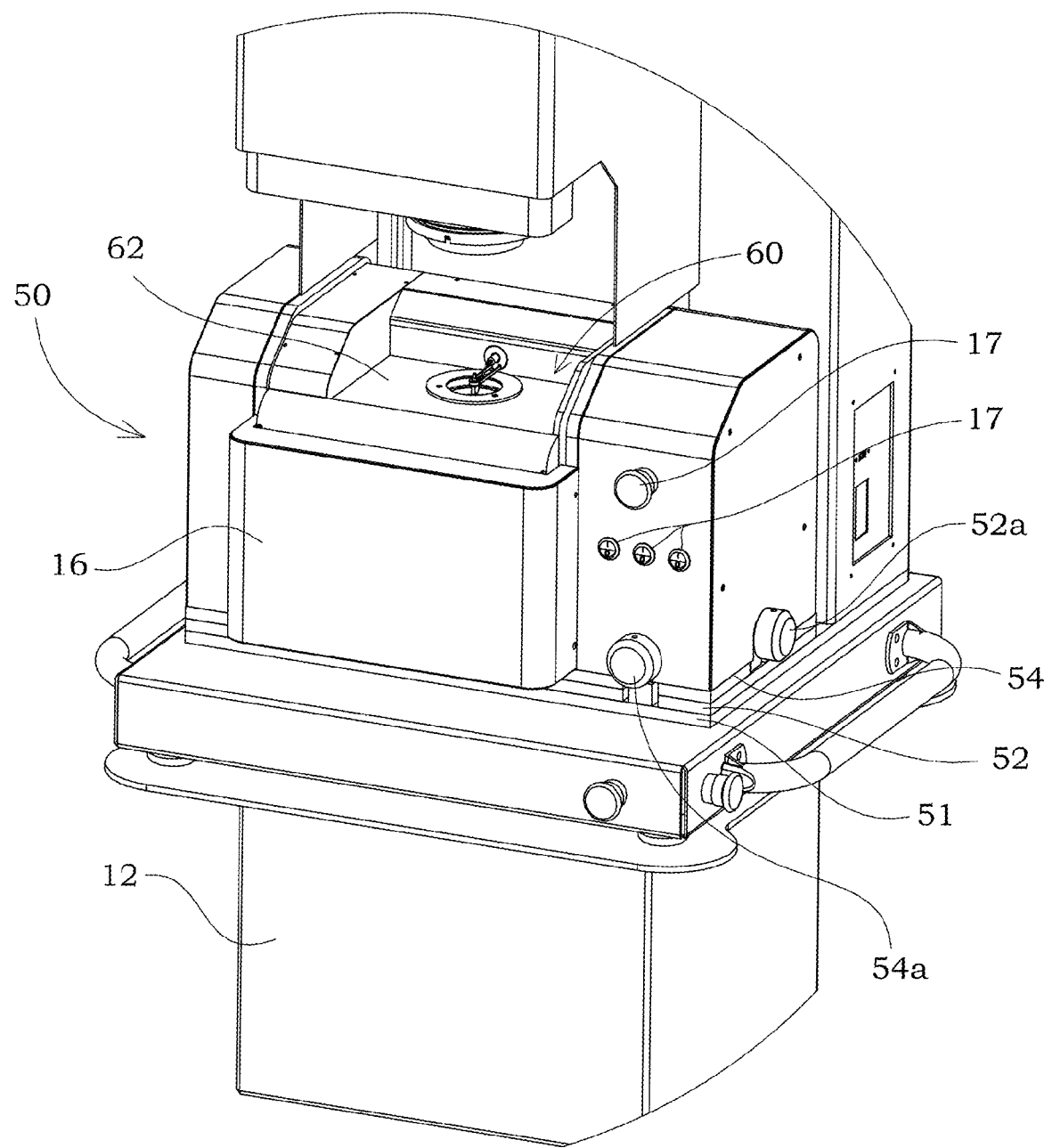
FIG. 3A provides a detailed front perspective view of the base of the illustrative embodiment of an imaging system.
Figure 3B:
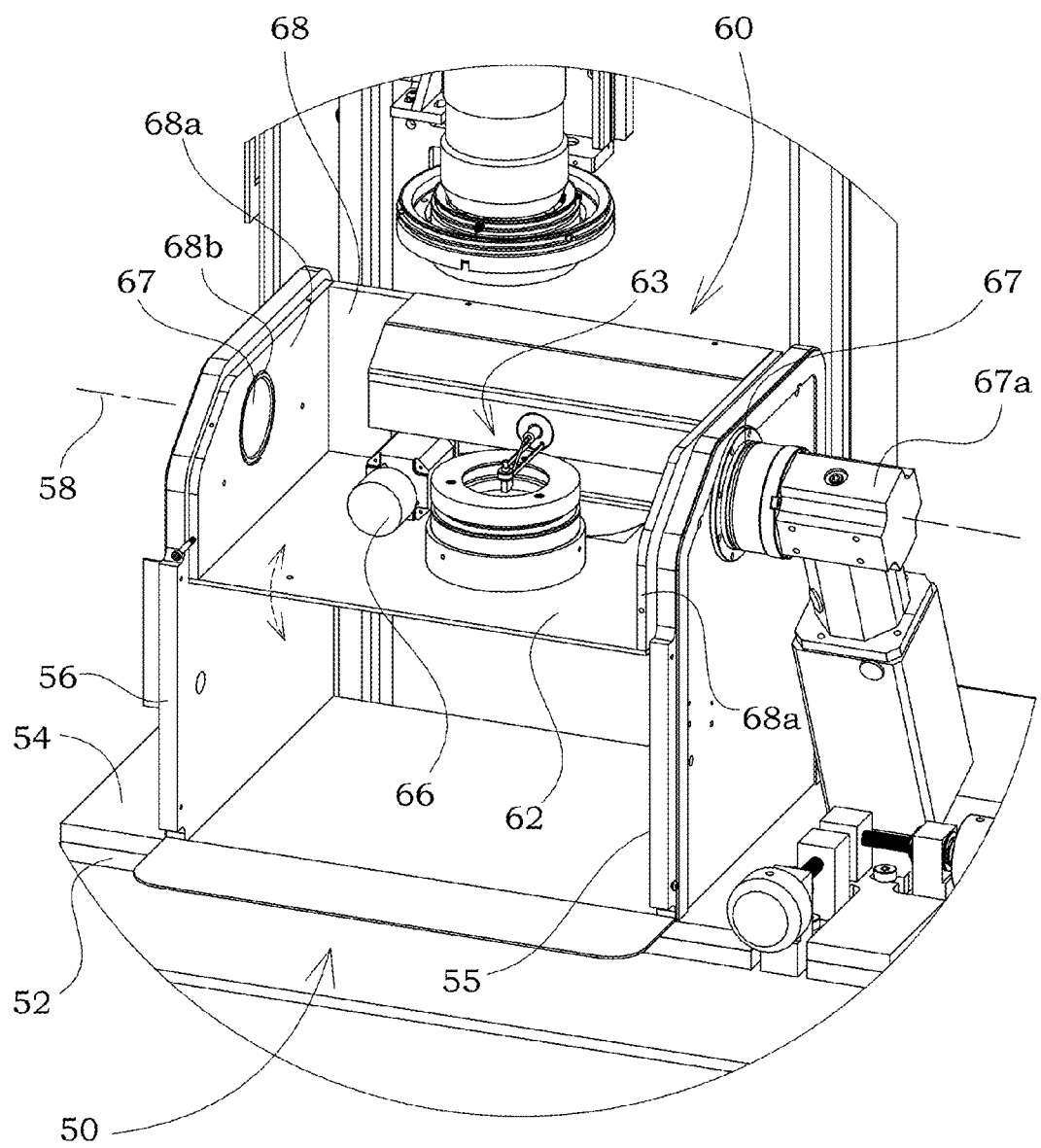
FIG. 3B provides a detailed front perspective view of the base of the illustrative embodiment of an imaging system with various components removed for clarity.

One embodiment of a base 50 that may be configured for use with the illustrative embodiment of the imaging system 10 is shown in perspective in FIG. 3A and in detail in FIG. 3B with the base cover 16 and base side covers 16a removed for clarity. As shown in FIG. 3A, one or more switches 17 may be positioned on a base side cover 16a and/or base cover 16. The base 50 may be supported by a base plate 51, on top of which an X-axis plate 52 and Y-axis plate 54 may be mounted.

The position of the base 50 components above the base plate 51 (and specifically, the stage 60) may be adjusted in a first dimension (i.e., the X-axis) via the X-axis adjustor 52a. Likewise, the position of the base components above the base 50 components above the base plate 51 may be adjusted in a second dimension (i.e., the Y-axis) via the Y-axis adjustor 54a. The X-axis and Y-axis adjustors 52a, 54a may be used to make fine adjustments in the position of the stage 60 (and consequently, the holder 63) with respect to the tower 14 (and consequently, with respect to the lens 30 and/or image capture device 20). It is contemplated that those adjustments will be most advantageous if available to adjust the position of the stage 60 in a horizontal plane, but the imaging system 10 is not so limited and the scope thereof extends to other adjustments of the base 50 components above the base plate 51, including but not limited to three-dimensional adjustments.

It is contemplated that the X-axis and Y-axis adjustor 52a, 54a may be configured as knobs having threaded shafts secured thereto. The threaded shaft of each adjuster 52a, 54a may then engage a corresponding threaded block secured to the corresponding plate 52, 54. Accordingly, in the illustrative embodiment of the imaging system 10, the adjusting the position of the X-axis plate 52 also causes the Y-axis plate 54 to move by the same amount in the X-axis. However, the base 50 may be configured so that adjusting the position of the Y-axis plate 52 does not affect a corresponding movement in the X-axis plate 52.

The optimal configuration for the capture device bracket 22, lens bracket 32, and illuminator bracket 42 will vary from one embodiment of the imaging system 10 to the next, and may vary based on application. Accordingly, the specific type of bracket 22, 32, 42 and/or configuration thereof is in no way limiting to the scope of the imaging system 10 as disclosed and claimed herein, and includes any bracket 22, 32, 42 that is configured to suitably engage the component for linear movement along at least one dimension.

Still referring to FIGS. 3A & 3B, the stage 60 may generally include a main platform 62. Two side plates 68a may extend upward from the main platform 62 on either side thereof. A back plate 68 may extend upward from the main platform 62 toward the back side of the main platform 62, which back plate 68 may be engaged with either side plate 68a. A holder 63 for engaging the subject gemstone may be positioned directly above a main platform 62, which main platform 62 may be configured with an aperture 62a therein. It is contemplated that the holder 63 may include a holder tip 63c configured as a vacuum pen to properly secure a subject gemstone within the imaging system 10. Such vacuum pens are generally well known in the art and therefore are not discussed further herein for purposes of brevity. Additionally, a bottom illuminator 61 may be engaged with the main platform 62, which bottom illuminator 61 may be configured in a manner similar to that previously described for the illuminator 40. In certain embodiments of the imaging system 10, the bottom illuminator may be configured as a dark field illuminator.

First and second mounts 55, 56 may extend upward from the X-axis plate 52 as shown in the illustrative embodiment, or from the base plate 51 and/or Y-axis plate 54 in other embodiments of the imaging system 10. The stage 60 may be pivotally engaged with the first and second mounts 55, 56 via two stage pivot points 67 on either side of the stage 60. A pitch motor 67a may be engaged with one or more tabs 68b, which tabs 68b may in turn be engaged with the side plates 68a to adjust the angle of the stage 60. This configuration allows the stage 60 (and consequently the holder 63) to pivot along a first axis 58 that may be horizontal with respect to the base 50 and tower 14. In the illustrative embodiment of the imaging system 10, the stage 60 may rotate along this axis by up to 360 degrees. As shown in FIG. 3B, the stage 60, holder 63, and main platform 62 may be configured so that the first axis 58 intersects the holder tip 63c, as further described below. It is contemplated that the pitch motor 67a may be electrically powered, but the imaging system 10 as disclosed and claimed herein is not so limited, and includes any suitable type of pitch motor 67a that functions to adjust the angle of the main platform 62 with respect to the base 50 and/or tower 14.

In the illustrative embodiment of the imaging system 10, the holder 63 may also pivot along a second axis with respect to the base 50 and the tower, wherein this second axis may be generally horizontal, and perpendicular to that provided via the first and second mounts 55, 56 and platform pivot points. Additionally, the second axis may intersect the first axis 58 at a point on or adjacent to the holder tip 63c. In the illustrative embodiment of the imaging system 10, this functionality may be achieved via engaging the various components that allow the holder 63 to pivot along the second axis with the stage 60, such that when the stage 60 rotates about the first axis 58, those components also rotate. In the illustrative embodiment of the imaging system 10, the holder 63 may rotate about this second axis by 360 degrees.

Figure 4:
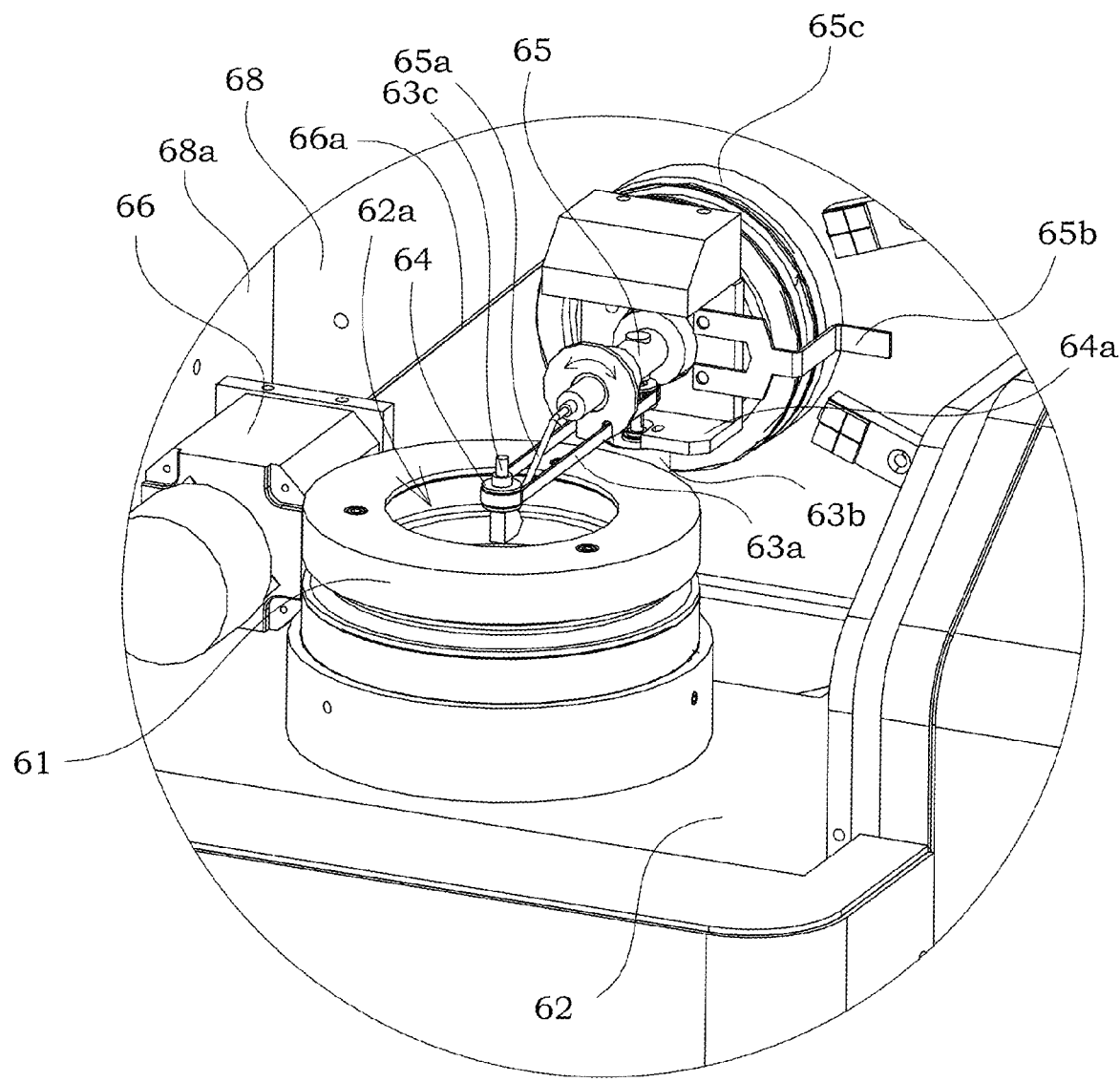
FIG. 4 provides a detailed view of the holder and holder mount and rotor of the illustrative embodiment of an imaging system.

As shown in FIG. 4, which provides a detailed view of several components of the base 50 and stage 60, a rotor 65 may be pivotally engaged with the back plate 68. To facilitate this pivotal engagement, a receiver 65c may be rotatably mounted to the back plate 68, wherein the axial position of the receiver 65c (and, consequently, the rotor 65) may be secured via one or more rotor brackets 65b. The receiver 65c may be configured to engage a rotor belt 66a, which rotor belt 66a may also be engaged with a roll motor 66. The roll motor 66 may be engaged with the main platform 62 and/or one side plate 68a. The roll motor 66 may provide a motive force to the holder 63 communicated thereto via the rotor belt 66a, receiver 65c, and rotor 65, respectively. It is contemplated that the roll motor 66 may be electrically powered, but the imaging system 10 as disclosed and claimed herein is not so limited, and includes any suitable type of roll motor 66 that functions to adjust the position of the holder 63 in a rotational manner.

A rotor arm 65a may extend from the rotor 65 to a holder mount 64 below the holder tip 63c. The rotor arm 65a may serve to communicate rotational and/or other forces from the rotor 65 to the holder tip 63c (and, consequently, to the subject gemstone engaged with the holder tip 63c) as well as provide structure support to those components. Additionally, if the holder tip 63c is configured as a vacuum pen, the rotor arm 65a may provide a conduit therefor from the vacuum source (not shown) to the holder tip 63c.

Other structures may be used to provide and/or communicate a rotational force to the holder 63 about a second axis, and the scope of the imaging system 10 as disclosed and claimed herein is in no way limited by the specific configuration, structure, and/or methods needed to accomplish such functionality. The rotor 65, rotor arm 65a, receiver 65c, rotor belt 66a, and roll motor 66 provide one illustrative embodiment of such a configuration, but are in no way limiting.

Still referring to FIG. 4, a yaw motor mount 64a may be engaged with a hub portion of the receiver 65c and/or the rotor bracket 65b. A yaw motor 63b may subsequently be engaged with the yaw motor mount 64a. A belt 63a may be engaged with the yaw motor 63b and a portion of the holder mount 64 such that rotational forces from the yaw motor 63b may be communicated to the holder mount 64 (and, consequently, the holder tip 63c) via the belt 63a. The resultant rotation of the holder mount 64 as a result of these forces may be along a third axis that is generally perpendicular to both the first axis 58 and second axis, and which third axis may be vertically oriented depending on the position of the stage 60. In the illustrative embodiment, the third axis may intersect the second axis and first axis 58 on or adjacent to the holder tip 63c. In the illustrative embodiment of the imaging system 10, the holder 63 may rotate about this third axis by 360 degrees.

As will be apparent to those skilled in the art in light of the present disclosure, the imaging system 10 may be configured so that the precise angle of this third axis may depend at least upon the position of the stage 60 about the first axis 58 and/or the position of the rotor 65 with respect to the back plate 68. Accordingly, the illustrative embodiment of the imaging system may allow a user to adjust the orientation of a subject gemstone engaged with the holder tip 63c in three-dimensional space via rotational about at least three different axes generally representing yaw, pitch, and roll dimensions. While these specific components are listed for one illustrative embodiment of the imaging system 10, it should be known that these are not the only components that may be used to achieve the desired result (namely, capturing images of a gemstone from three hundred and sixty degree viewing angles (360°) about at least one axis of rotation). For example, it is known to incorporate various gemstone holding devices such as tweezers, prongs, or the like as opposed to the holder tip 63c as shown in the illustrative embodiment.

Other structures may be used to provide and/or communicate a rotational force to the holder tip 63a about a third axis, and the scope of the imaging system 10 as disclosed and claimed herein is in no way limited by the specific configuration, structure, and/or methods needed to accomplish such functionality. The yaw motor 63b, yaw motor mount 64a, and belt 63a provide one illustrative embodiment of such a configuration, but are in no way limiting.

As it should be appreciated by one of ordinary skill in the art, a variety of gemstones or precious stones may be used with the imaging system 10. While the illustrative embodiment of the imaging system 10 allows a user to adjust the orientation of a subject gemstone about yaw, pitch, and roll dimensions, to make precision adjustments to the position of the gemstone via the Y-axis and X-axis adjustors 52a, 54a, and the relative position between the subject gemstone and an image capture device 20, lens 30, and/or illuminator 40 it should be obvious to one or ordinary skill in the art in light of the present disclosure that many other methods and/or structures for adjusting the position and/or orientation of the subject gemstone relative the image capture device 20 (or for adjusting the position of the image capture device 20 relative the subject gemstone) may be employed without departing from the spirit and scope of the imaging system 10 and associated method as disclosed and claimed herein. In light of the present disclosure, those skilled in the art will also appreciate that the imaging system 10 and associated method as disclosed and claimed herein may employ multiple image capture devices 10, which may be used to capture images and/or video of subject gemstones at different angles simultaneously. Additionally, the illustrative embodiment of the imaging system 10 as shown herein may include a high resolution image capture device 20 configured to capture both still and video images. The system may use a computer viewing program to display the captured images and videos.

2. General Description of Operation

It is contemplated that the various moving components of the imaging system 10 may be controlled via a CPU (not shown) in communication with the imaging system 10. It is contemplated that information from the image capture device 20 may be communicated to and stored on this CPU or another data storage device in communication with the imaging system 10 and/or this CPU. Additionally, it is contemplated that the imaging system 10 may operate according to a pre-programmed computer code (software program) to capture images of a subject gemstone. The computer code (software program) may be used to control the various moving components of the imaging system 10 and the image capture device 20. For example, a user may position a subject gemstone atop the holder tip 63c for securely holding the subject gemstone. The user may then manipulate the Y-axis and X-axis adjustors 52a, 54a so that the subject gemstone is properly positioned in a generally horizontal plane with respect to the image capture device 20. At this point, the desired focal depth of the image capture device 20 may be determined (e.g., 15 centimeters from the end of the lens 30). Finally, the user may initiate the imaging process via the CPU.

Once initiated, the imaging process may be fully automatic as controlled by the computer code residing on the CPU in communication with the imaging system 10. For example, in an initial position, the stage 60 and the holder tip 63c may be oriented perpendicular with respect to the base plate 51 (x-y plane) such that the imaging device 20 captures aerial views of the subject gemstone's table, wherein the focal depth is at the exterior surface of the subject gemstone's table. The imaging device 20 may capture multiple images and/or video from this angle under varied lighting conditions, magnifications, and/or any other conditions the user specifies, which may include but is not limited to manipulating the position of the illuminator 40, the number of illuminator segments 41 utilized, the number of lumens emitted from the illuminator 40, bottom illuminator 61, and/or color of light the illuminator 40 emits.

The CPU may then direct the image capture device positioner 26 to move a predetermined distance along the capture device track 24 (which may generally be the Z-axis) so that the focal depth is at an interior position within the subject gemstone (e.g., 0.2 millimeters below the exterior surface of the table). Again, the imaging device 20 may capture multiple images and/or video from this angle under varied lighting conditions, magnifications, and/or any other conditions the user specifies, which may include but is not limited to manipulating the position of the illuminator 40, the number of illuminator segments 41 utilized, the number of lumens emitted from the illuminator 40, and/or color of light the illuminator 40 emits. The number of images associated with a subject gemstone will depend on the specific application, and may vary at least according to the data storage space available for storing images and/or video and the bandwidth associated with the imaging system 10 and device on which the image information is stored. It is contemplated that for many applications a sufficient number of images will be the number required to approximately allow a user to emulate a microscope, i.e., locate various features of the subject gemstone in three-dimensional space based on the images the imaging system 10 collects for that subject gemstone.

At any focal depth the orientation of the subject gemstone may be varied via the angle of its yaw, pitch, and/or roll using the yaw motor 63b, roll motor 66, and/or pitch motor 67a and associated components as previously described in detail. It is contemplated that the user may control these components via the CPU in communication with the imaging system 10. Once the desired number and/or type of images and/or videos of the subject gemstone have been captured for a given angle and/or focal depth, the orientation of the gemstone may be changed and the image capture device 20 may then repeat the imaging process from this new angle and/or focal depth under varied lighting conditions, magnifications, and/or any other conditions the user specifies, which may include but is not limited to manipulating the position of the illuminator 40, the number of illuminator segments 41 utilized, the number of lumens emitted from the illuminator 40, and/or color of light the illuminator 40 emits.

The imaging system 10 may repeat this process several times, adjusting the orientation of the subject gemstone and/ or focal depth each time. Due to the number of viewing angles between the image capture device 20 and subject gemstone may possible by the imaging system 10, the illustrative embodiment of the imaging system 10 may capture images of the subject gemstone from virtually any angle.

An infinite number and/or types of algorithms incorporated into the computer code (software program) to automate the imaging system 10 exist, and accordingly the scope of the imaging system 10 and/or viewer system 100 is in no way limited thereby. One illustrative embodiment incorporates a three-dimensional matrix of images corresponding to focal points on the subject gemstone in three-dimensional space. The distance between the focal points in the vertical and/or horizontal dimensions may be determined by the user and/or programmer, and may vary based on multiple factors, including but not limited to digital storage space and/or bandwidth. Once the general profile of the gemstone has been determined (e.g., type of cut, general dimensions of gemstone, which may be manually input or determined via the computer code controlling the imaging system 10), a starting focal point may be assigned. Each focal point may be relative to that focal point and assigned a value based on the starting focal point. In one example, Cartesian coordinates may be used such that the starting focal point is assigned a value of 0, 0, 0. The next focal point to the right of the starting focal point may be assigned a value of 1, 0, 0, the next focal point in front the starting focal point may be assigned a value of 0, 1, 0, and the next focal point above the starting focal point may be assigned a value of 0, 0, 1. This is but one example of a method for organizing data for a gemstone collected via the imaging system 10, and is in no way limiting to the scope thereof.

The functionality of the illustrative embodiment of the imaging system 10 allows the image capture device 20 to view the subject gemstone. In one embodiment of using the imaging system 10, the stage 60 may be initially at rest in the x-y plane. During image and/or video capture, the stage 60 may rotate about the first axis 58 to capture additional viewing angles of the subject gemstone.

While the illustrative embodiment of the imaging system 10 allows the user to adjust the orientation of a subject gemstone about its yaw, pitch, and roll axes and the relative distance between the subject gemstone and the image capture device 20 by moving the image capture device 20, this is in no way limits to the scope of the imaging system 10. Any method or combination of capturing images by moving an image capture device 20 or a plurality of image capture device 20 relative to a subject gemstone or vice versa may be used without departing from the scope of this imaging system 10. For example, under a second embodiment, a subject gemstone may held in place by a vacuum pen or other device for stabilizing a gemstone while still promoting visual access to a majority of the gemstone's surface area, wherein the position of the vacuum pen is constant and an image capture device 20 or plurality thereof move relative to the subject gemstone while collecting images thereof. The position of the image capture device 20 or plurality thereof could be manipulated manually or could be controlled by an automated computer program residing on a CPU in communication with the imaging system 10.

3. General Description of Information Retrieval

Figure 5:
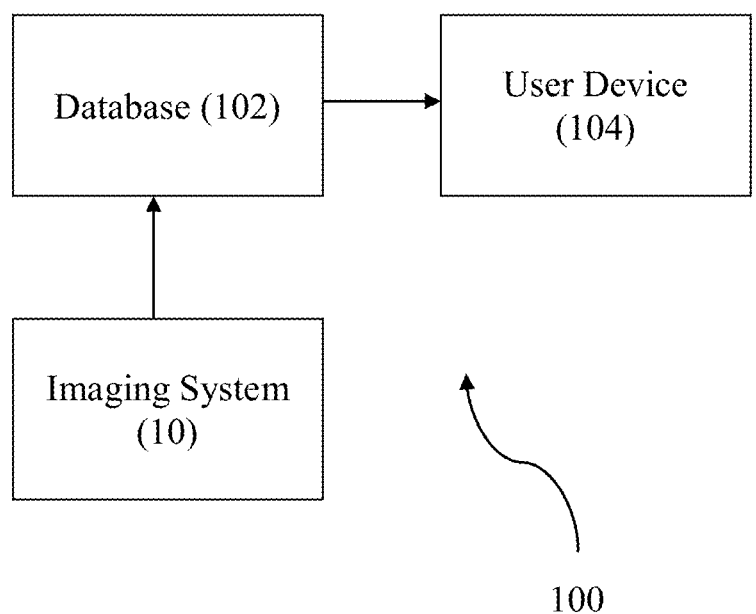
FIG. 5 provides a schematic view of an illustrative embodiment of a viewer system that may be used in conjunction with the imaging system disclosed herein.

The imaging system 10 may be configured for use with a viewer system 100. A schematic of an illustrative embodiment of a viewer system 100 is shown in FIG. 5. As shown, the imaging system 10 may be in communication with a database 102. Images for a subject gemstone may be communicated from the imaging system 10 to the database 102 and catalogued so that multiple images associated with a plurality of specific gemstones may be stored on the database 102. The database 102 may be remotely accessible by a user device 104 (e.g., smart phone, laptop, smart television, etc.) so that a user may retrieve the information associated with a specific gemstone. It is contemplated that the user device 104 may access the database 102 via a secure web portal (not shown), but the viewer system 100 as disclosed herein is not so limited.

The user may select a specific gemstone based on various criteria (including but not limited to various certifications (e.g., Gemological Institute of America Certification) for gemstone grades. After selecting a specific gemstone, the user may then have access to certain information related to that specific gemstone, which information may be in the form of various digital images captured using the imaging system 10 and saved to a CPU or database 102 in communication with the imaging system 10 and/or the user device 104. It will be understood that information from the imaging system 10 may pass through other types of hardware and/or undergo additional processing before it is deposited on the database 102, though such steps and/or hardware are not shown herein for purposes of clarity.

Figure 6A:
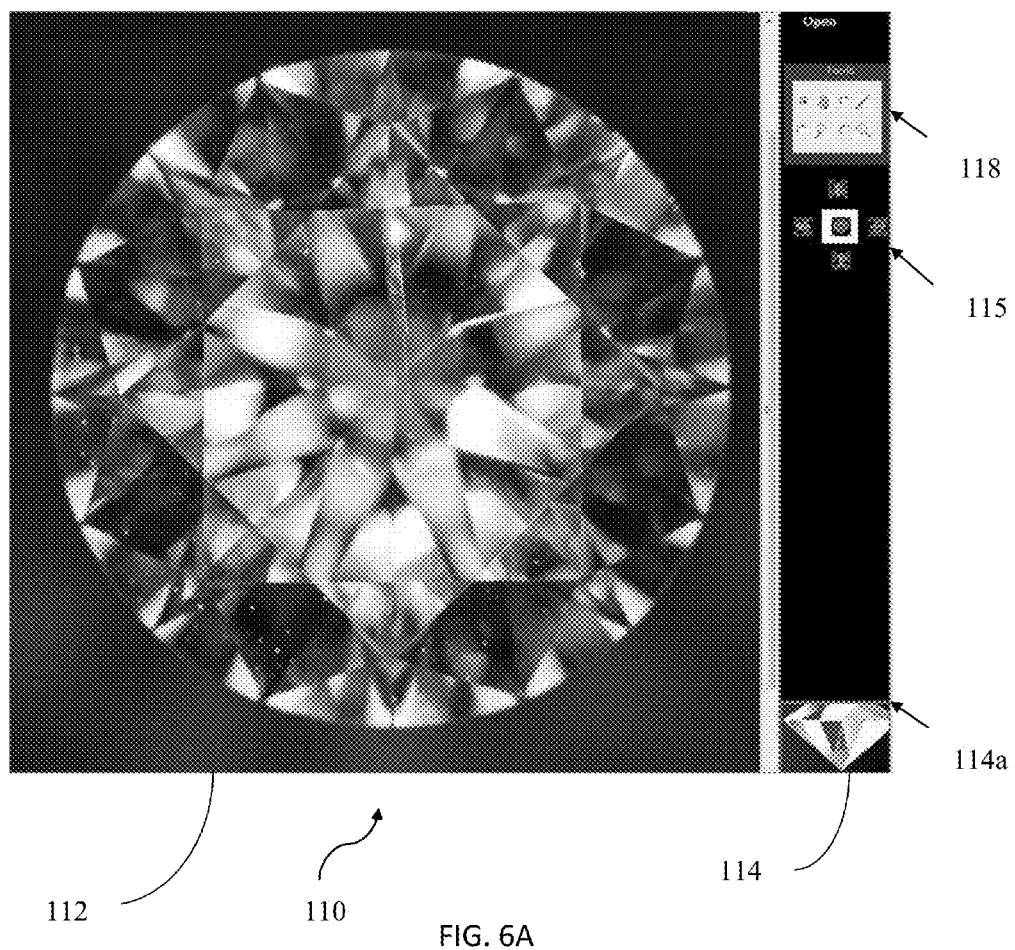
FIG. 6A provides a first sample screen shot from an illustrative embodiment of a GUI for one viewer system that may be used with the imaging system.
Figure 6B:
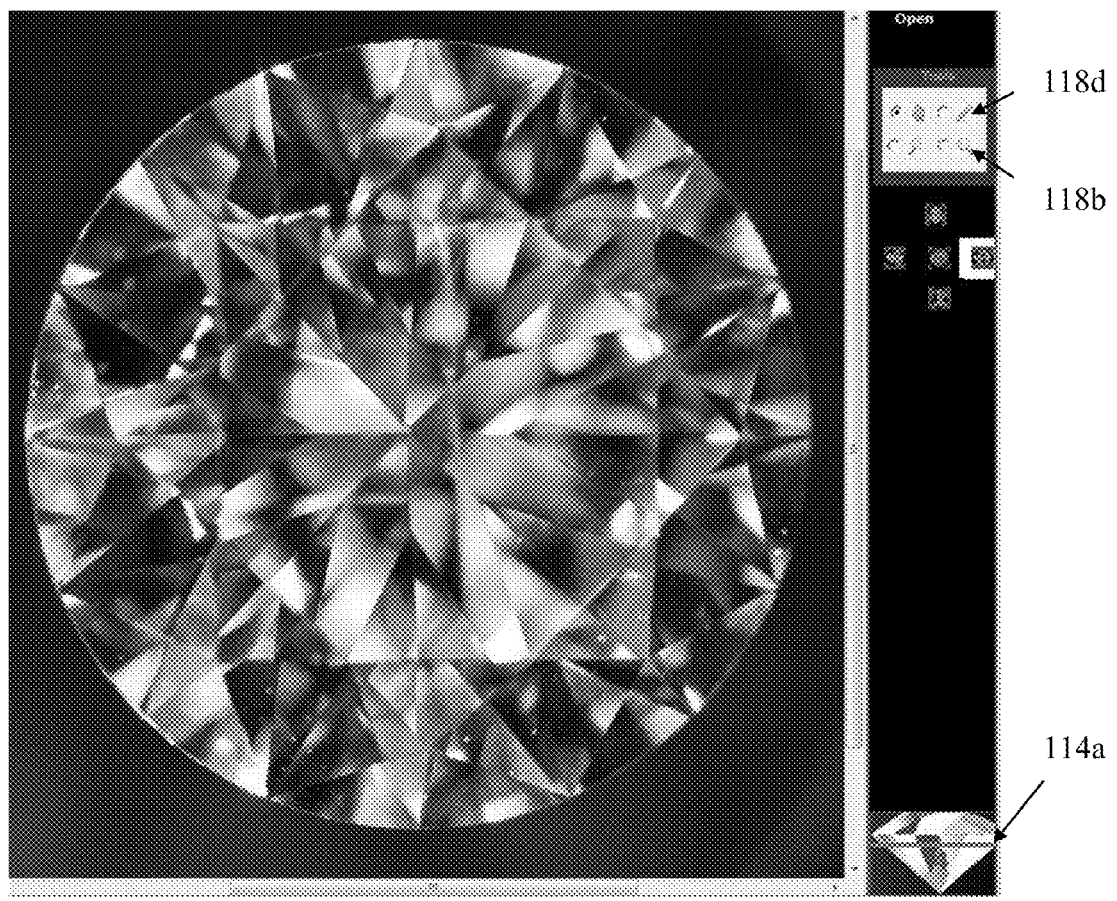
FIG. 6B provides a second sample screen shot from an illustrative embodiment of a GUI for one viewer system that may be used with the imaging system.

A first view of an illustrative graphic user interface (GUI) 110 that may be displayed on a user device 104 via the viewer system is shown in FIG. 6A. The computer code (software program) powering the GUI 110 may reside on the database 102 and/or another computing device (e.g., server) that may be in communication with the database 102 and a user device 104. Once a user has selected a specific gemstone, various thumbnail images of that gemstone may be displayed in the image selector 115 portion of the GUI 110. When a user selects a specific thumbnail image form the image selector 115, an enlarged, higher resolution image corresponding to that thumbnail image may be displayed in the main pane 112. The thumbnail images in the image selector 115 may correspond to images of the specific gemstone with the table thereof at various angles with respect to the image capture device 20 and/or at various focal depths. An orientation indicator 114 may be provided on the GUI 110, wherein a focal depth line 114a shows the depth at which the image capture device 20 was in focus. For example, the image in the main pane 112 shown in FIG. 6A is generally focused at the top surface of the table, so the focal depth line 114a is accordingly positioned as shown in the orientation indicator 114. However, the image in the main pane 112 shown in FIG. 6B is generally focused at predetermined distance below the table, as shown by the focal depth line 114a in FIG. 6B.

The GUI 110 may also include a tool selector 118. The tool selector may allow the user to select a zoom in 118a feature, wherein the user may zoom in on a specific area of the main pane 112 for further details of the specific gemstone. The tool selector may also include a zoom out feature 118b to allow the user to view the specific gemstone from a broader vantage. The tool selector 118 may also include a pan 118c that allows the user to move the image left/right and/or up/down within the main pane 112. Finally, the tool selector 118 may also include a markup 118d that may allow the user to circle and/or otherwise draw attention to specific areas of the image in the main pane 112.

Figure 6C:
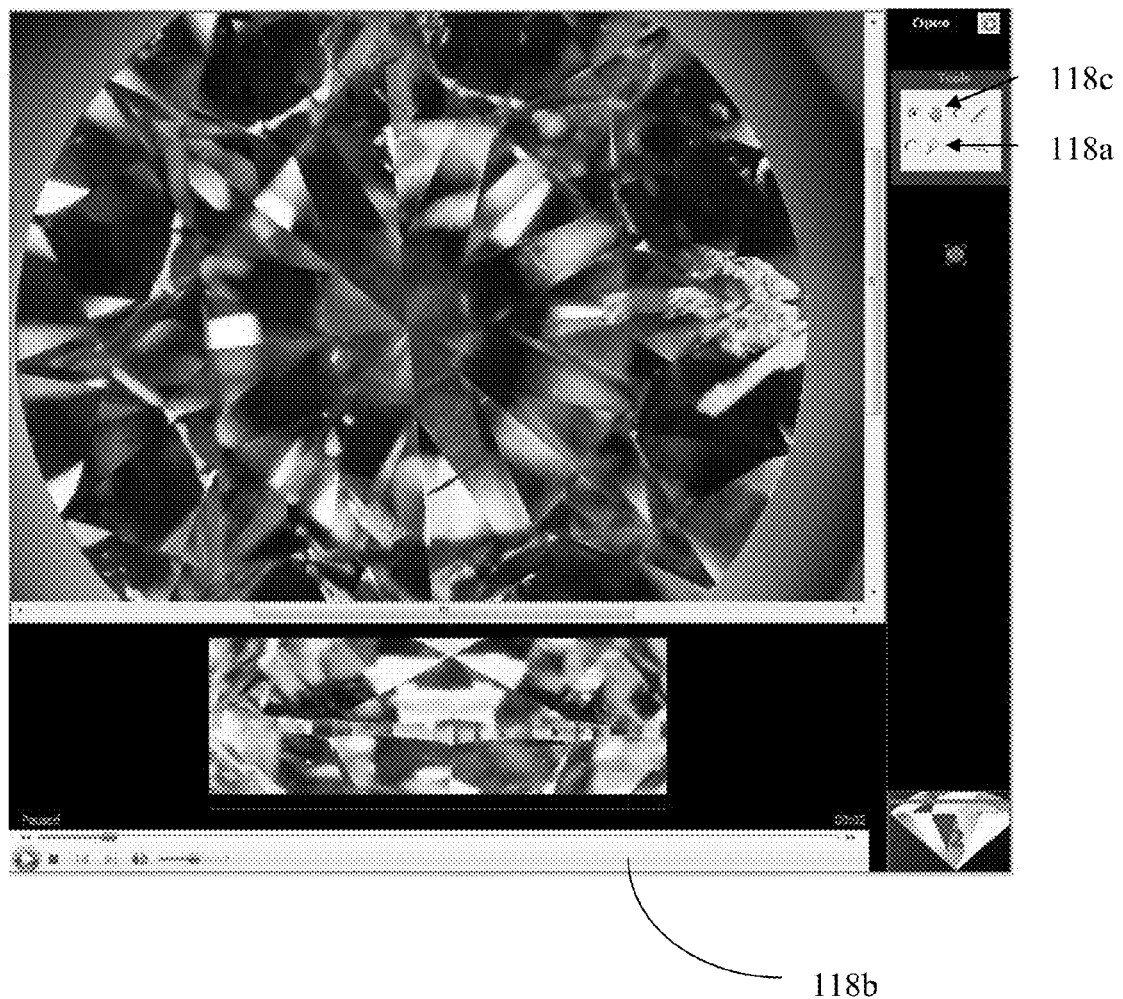
FIG. 6C provides a third sample screen shot from an illustrative embodiment of a GUI for one viewer system that may be used with the imaging system.

The GUI 110 may also include a video pane 116 positioned below the main pane 112, as shown in FIG. 5C. The video pane 116 may provide video images captured by the imaging system 10 for the specific gemstone. For example, in the embodiment shown in FIG. 6C, the imaging device 10 captured video of the girdle of the subject gemstone rotating about an axis passing through the center of the table, which video may be displayed in the video pane 116 of the GUI 110.

Because the method by which the imaging system 10 captures images and/or video of a subject gemstone may be automated, all gemstones may be capable of side-by-side comparison using the viewer system 100. A user may view two or more gemstones according to the exact same specifications (i.e., magnification level, lighting conditions, angle of view, focal depth etc.). A user device 104 may access the database 102 of information and images for a specific gemstone such that when a user selects that gemstone from the database 102, the user may view images of that specific gemstone according to various options, including but not limited to magnification of the gemstone to see defects at varying internal gemstone depths, actual simulation of lighting to display the gemstone's reflective capacity under sunlight, office lighting, etc.

According to the present disclosure, the imaging system 10 and/or viewer system 100 may allow a user to gathering the same visual information about a specific gemstone as if the user had physical possession of the gemstone and was viewing that gemstone through a microscope. That is, the present disclosure provides a microscope emulator, which may allow a user to subjectively rate a gemstone in ways not possible through simply selecting various certified grade value criteria (i.e., cut, color, clarity, and/or carat specifications).

For example, a certain gemstone may have a clarity grading of $I_1$ per GIA standards due to an inclusion, which (based on the gemstone grade certificate alone) some customers may find undesirable. However, given the opportunity to examine such a gemstone under a microscope, a trained individual may be able to orient such a gemstone so that the inclusion is positioned behind a prong or other structure of a setting to minimize any visual impact of the inclusion. This type of analysis is not possible by simply looking at the certified grade values for the specific gemstone, but traditionally requires physical possession of the gemstone for examination in a microscope. The present disclosure allows this type of examination remotely, so as to dispatch with shipping of gemstones, and the costs and time delays associated therewith.

According to the present disclosure, it is contemplated that the imaging system 10 and viewer system 100 may facilitate the implementation of a distribution system of gemstones, wherein users may evaluate gemstones for purchase via a secure, online web portal (which may be configured as a viewer system 100 as described herein). The distribution system may allow users to buy and/or sell specific gemstones via uploading certain information related to the gemstone (e.g., GIA certification sheet, images captured from the imaging system 10, etc.) and allowing other users access to that information.

The distribution system may include an authentication module, which may be integrated into the viewing system 100, or which may be separate therefrom. The authentication module may require a user to first register for an account, during which registration various information about the user is provided (e.g., name, EIN or SSN, address, licensures, etc.). After proper review, the user may be issued a username and password that the user may use to log on to the distribution system or viewer system 100.

Having described the preferred and illustrative embodiments, other features, advantages, and/or efficiencies of the imaging system 10 and/or viewer system 100 and associated methods will undoubtedly occur to those of ordinary skill in the art, as will numerous modifications and alterations of the disclosed embodiments and methods, all of which may be achieved without departing from the spirit and scope of the imaging system 10, viewer system 100, and/or associated methods. Furthermore, the imaging system 10, viewer system 100, and/or associated methods are not limited to the specific embodiments pictured and described herein, but are intended to apply to all similar methods and apparatus for capturing, reproducing, and/or viewing images. Accordingly, modifications and alterations from the disclosed embodiments will occur to those skilled in the art without departure from the spirit and scope of the imaging system 10, viewer system 100, and/or associated methods.

What is claimed is:

1. An imaging system comprising:
   a. a tower;
   b. a base engaged with said tower;
   c. an image capture device moveable in a first dimension with respect to said tower;
   d. a stage pivotally engaged with said base about at least one stage pivot point, wherein a first axis of rotation between said stage and said base about said at least one stage pivot point is generally horizontal;
   e. a holder engaged with said stage, wherein said holder is configured to secure the position of a gemstone, wherein said holder is rotatable with respect to said stage about a second axis of rotation between said stage and said holder that is generally horizontal and generally perpendicular to said first axis of rotation, wherein a portion of said holder is rotatable with respect to said stage about a third axis of rotation between said stage and said holder that is generally vertical and generally perpendicular to both said first and second axes of rotation, and wherein said first, second, and third axes of rotation intersect at a common point;
   f. a capture device track secured to said tower;
   g. a first capture device bracket slidably engaged with said capture device track, wherein said image capture device is engaged with said capture device bracket;
   h. a lens track secured to said first capture device bracket;
   i. a lens bracket slidably engaged with said lens track;
   j. a lens secured to said lens bracket, wherein said lens is in communication with said image capture device;
   k. a main platform that is generally rectangular in shape;
   l. a first side plate secured to a first end of said main platform and extending upward therefrom;
   m. a second side plate secured to a second end of said main platform and extending upward therefrom;
   n. a back plate engaged with a back edge of said main platform extending upward therefrom, wherein said first and second side plates and said back plate are engaged with one another;
   o. a rotor pivotally engaged with said back plate, wherein said second axis of rotation is provided via the pivotal engagement between said rotor and said back plate;
   p. a rotor arm engaged with said rotor;
   q. a holder mount engaged with a distal end of said rotor arm; and,
   r. a holder tip pivotally engaged with said holder mount, wherein said holder tip is configured for direct engagement with a gemstone, and wherein said third axis of rotation is provided via the pivotal engagement between said holder tip and said rotor arm.

2. The imaging system according to claim 1 further comprising:
   a. a capture device track secured to said tower;
   b. a first capture device bracket slidably engaged with said capture device track, wherein said image capture device is engaged with said capture device bracket.

3. The imaging system according to claim 1 further comprising:
   a. a lens track secured to said first capture device bracket;
   b. a lens bracket slidably engaged with said lens track; and
   c. a lens secured to said lens bracket, wherein said lens is in communication with said image capture device.

4. An imaging system comprising:
   a. a tower extending upward, wherein said tower comprises:
      i. a capture device track engaged with said tower and generally oriented vertically;
      ii. a capture device bracket slidably engaged with said capture device track;
      iii. an image capture device engaged with said capture device bracket;
      iv. a lens track engaged with said capture device bracket and generally oriented vertically;
      v. a lens bracket slidably engaged with said lens track;
      vi. a lens engaged with said lens bracket;
   b. a base engaged with said tower, wherein said base comprises
      i. a base plate;
      ii. a first mount engaged with said base plate and extending upward therefrom;
      iii. a second mount engaged with said base plate and extending upward therefrom;
      iv. a stage pivotally engaged with said base about a first axis, said stage comprising:
         1. a main platform generally rectangular in shape;
         2. a first side plate secured to a first end of said main platform and extending upward therefrom, wherein said first side plate is pivotally engaged with said first mount;
         3. a second side plate secured to a second end of said main platform and extending upward therefrom, wherein said second side plate is pivotally engaged with said second mount;
         4. a back plate engaged with a back edge of said main platform extending upward therefrom, wherein said first and second side plates and said back plate are engaged with one another;

v. a holder engaged with said base, said holder comprising:
1. a rotor pivotally engaged with said back plate, wherein said the pivotal engagement between said rotor and said back plate creates a second axis of rotation, said second axis of rotation defined as between said rotor and said back plate;
2. a rotor arm engaged with said rotor and extending therefrom;
3. a holder mount engaged with a distal end of said rotor arm; and,
4. a holder tip pivotally engaged with said holder mount, wherein said holder tip is configured for direct engagement with a gemstone, and wherein the pivotal engagement between said holder tip and said rotor arm creates a third axis of rotation, said third axis of rotation defined as between said holder tip and said holder mount.

5. The imaging system according to claim 4 further comprising a capture device bracket positioner engaged with said capture device bracket, wherein said capture device bracket positioner is configured to move said capture device bracket along said capture device track.

6. The imaging system according to claim 5 further comprising a lens bracket positioner engaged with said lens bracket, wherein said lens bracket positioner is configured to move said lens bracket along said lens track.

7. The imaging system according to claim 6 further comprising:
a. an illuminator track engaged with said tower and generally oriented vertically;
b. an illuminator bracket slidably engaged with said illuminator track;
c. an illuminator secured to said illuminator bracket;
d. an illuminator bracket positioner engaged with said illuminator bracket, wherein said illuminator bracket positioner is configured to move said illuminator bracket along said illuminator track.

8. The imaging system according to claim 7 further comprising:
a. an X-axis plate slidably engaged with said base plate along a first dimension;
b. a Y-axis plate slidably engaged with said X-axis plate along a second dimension, wherein said first and said second dimensions are generally perpendicular to one another.

9. The imaging system according to claim 8 further comprising a pitch motor engaged with a first stage pivot point adjacent a pivotal interface between said first side plate and said first mount, wherein said pitch motor is configured to cause said stage to rotate with respect to said base about said first axis.

10. The imaging system according to claim 9 further comprising:
a. a roll motor engaged with said stage;
b. a receiver engaged with said rotor;
c. a rotor bracket configured to pivotally engaged said receiver and said stage; and,
d. a rotor belt configured to communicate rotational energy from said roll motor to said receiver.

11. The imaging system according to claim 10 further comprising:
a. a yaw motor mount engaged with said stage;
b. a yaw motor engaged with said yaw motor mount; and
c. a belt configured to communicate rotational energy from said yaw motor to said holder tip.

12. The imaging system according to claim 10 wherein said first, second, and third axes of rotation intersect at a common point on said holder tip.

* * * * *